(12) United States Patent
Jongen

(10) Patent No.: US 8,748,852 B2
(45) Date of Patent: *Jun. 10, 2014

(54) COMPAC GANTRY FOR PARTICLE THERAPY

(71) Applicant: Yves Jongen, Louvain-la-Neuve (BE)

(72) Inventor: Yves Jongen, Louvain-la-Neuve (BE)

(73) Assignee: Ion Beam Applications, SA, Louvain-la-Neuve (BE)

( * ) Notice: Subject to any disclaimer, the term of this patent is extended or adjusted under 35 U.S.C. 154(b) by 0 days.

This patent is subject to a terminal disclaimer.

(21) Appl. No.: 13/737,867

(22) Filed: Jan. 9, 2013

(65) Prior Publication Data

US 2013/0187060 A1 Jul. 25, 2013

Related U.S. Application Data

(63) Continuation of application No. 13/498,131, filed on Mar. 23, 2012, which is a continuation of application No. PCT/EP2010/064155, filed on Sep. 24, 2010.

(30) Foreign Application Priority Data

Sep. 28, 2009 (EP) .................................... 09171550

(51) Int. Cl.
*H01J 3/26* (2006.01)

(52) U.S. Cl.
USPC ...................................................... 250/492.3

(58) Field of Classification Search
USPC ........................................... 250/492.1, 492.3
See application file for complete search history.

(56) References Cited

U.S. PATENT DOCUMENTS

| 4,812,658 | A * | 3/1989 | Koehler .................... 250/396 R |
| 6,476,403 | B1 * | 11/2002 | Dolinskii et al. .......... 250/492.3 |
| 6,774,383 | B2 * | 8/2004 | Norimine et al. .......... 250/505.1 |
| 7,834,336 | B2 * | 11/2010 | Boeh et al. ................. 250/505.1 |
| 8,063,381 | B2 * | 11/2011 | Tsoupas et al. ......... 250/396 ML |
| 2002/0033456 | A1 * | 3/2002 | Tachikawa et al. ........... 250/398 |
| 2004/0113099 | A1 * | 6/2004 | Eickhoff et al. ........... 250/492.3 |
| 2004/0159795 | A1 * | 8/2004 | Kaercher et al. .......... 250/396 R |
| 2007/0262269 | A1 * | 11/2007 | Trbojevic .................. 250/492.3 |
| 2008/0023644 | A1 * | 1/2008 | Pedroni ........................ 250/400 |
| 2008/0067452 | A1 * | 3/2008 | Moriyama et al. ......... 250/503.1 |
| 2010/0038552 | A1 * | 2/2010 | Trbojevic ................ 250/396 ML |
| 2010/0320403 | A1 * | 12/2010 | Amaldi et al. ............. 250/492.3 |
| 2011/0101235 | A1 * | 5/2011 | Iwata ....................... 250/396 ML |
| 2011/0101236 | A1 * | 5/2011 | Cameron et al. ....... 250/396 ML |
| 2011/0266464 | A1 * | 11/2011 | Takai et al. ................ 250/492.1 |
| 2013/0001432 | A1 * | 1/2013 | Jongen ...................... 250/396 R |
| 2013/0105703 | A1 * | 5/2013 | Harada et al. .......... 250/396 ML |
| 2013/0289330 | A1 * | 10/2013 | Haruna et al. .................... 600/1 |

FOREIGN PATENT DOCUMENTS

WO WO 2008081480 A1 * 7/2008

OTHER PUBLICATIONS

Anferov, Vladimir "Combined X-Y Scanning Magnet for Conformal Proton Radiation Therapy" Med. Phys. 32 (3), Mar. 2005.*

* cited by examiner

*Primary Examiner* — Nicole Ippolito
*Assistant Examiner* — Wyatt Stoffa
(74) *Attorney, Agent, or Firm* — Christopher Casieri

(57) ABSTRACT

The present invention relates to a particle therapy apparatus used for radiation therapy. More particularly, this invention relates to a compact isocentric gantry for delivering particle beams perpendicularly to a rotation axis of the gantry. The gantry comprises three dipole magnets. The angle of the last dipole magnet is smaller than 90° and a most preferred bending angle for this last dipole magnet is 60°.

21 Claims, 8 Drawing Sheets

COMPAC GANTRY FOR PARTICLE THERAPY

This application is a Continuation of U.S. application Ser. No. 13/498,131 filed on Mar. 23, 2012, which is a Continuation of international application PCT/EP2010/064155, filed Sep. 24, 2010, which in turn claims priority to European Patent Application No. 09171550.8, filed on Sep. 28, 2009.

FIELD OF THE INVENTION

The present invention relates to a charged particle therapy apparatus used for radiation therapy. More particularly, this invention relates to a compact gantry for delivering particle beams.

STATE OF THE ART

Radiotherapy using charged particles (e.g. protons, carbon ions, . . . ) has proven to be a precise and conformal radiation therapy technique where a high dose to a target volume can be delivered while minimizing the dose to surrounding healthy tissues. A particle therapy apparatus comprises an accelerator producing energetic charged particles, a beam transport system for guiding the particle beam to one or more treatment rooms and, for each treatment room, a particle beam delivery system. One can distinguish between two types of beam delivery systems, fixed beam delivery systems delivering the beam to the target from a fixed irradiation direction and rotating beam delivery systems capable of delivering beam to the target from multiple irradiation directions. Such a rotating beam delivery system is further named a gantry. The target is generally positioned at a fixed position defined by the crossing of the rotation axis of the gantry and the central beam axis. This crossing point is called isocenter and gantries of this type capable of delivering beams from various directions to the isocenter are called isocentric gantries.

The gantry beam delivery system comprises devices for shaping the beam to match the target. There are two major techniques used in particle beam therapy to shape the beam: the more common passive scattering techniques and the more advanced dynamic radiation techniques. An example of a dynamic radiation technique is the so-called pencil beam scanning (PBS) technique. In PBS, a narrow pencil beam is magnetically scanned on a plane orthogonal to the central beam direction. Lateral conformity in the target volume is obtained by adequate control of the scanning magnets. By varying the energy of the particle beam, different layers in the target volume, characterized by their fixed particle energy, can subsequently be irradiated. In this way, particle radiation dose can be delivered to the entire 3D target volume.

The particle beam energies required to have sufficient penetration depth in the patient depend on the type of particles used. For example, for proton therapy, beam energies are typically ranging between 70 MeV and 250 MeV. The applicant has built proton gantries for use with proton beam energies up to 235 MeV. Such a gantry is shown in FIG. 1A and this gantry configuration is described by J. B. Flanz in "Large Medical Gantries", Proceedings of the 1995 Particle Accelerator Conference, Volume 3, p 2007-2008. In this gantry, the beam is first focused by a series of quadrupoles before being deflected through a 45° dipole magnet 12, the beam is then further focused by 5 quadrupole magnets 19 before it is bent through a 135° dipole magnet 15 and directed towards the isocenter (perpendicular to the axis of rotation). This gantry comprises also two scanning magnets 18 to scan the beam in two orthogonal directions for use with pencil beam scanning Thanks to the large distance of 3 m between the last bending magnet of 135° and the isocenter, these scanning magnets 18 are mounted downstream from the last bending magnet. Between the last bending magnet 15 and the scanning magnets 18 two additional quadrupole magnets 19 are installed. The drawback of this gantry is that it has large dimensions: a diameter of about 10 m and a length of more than 10 m. This gantry has also a large manufacturing cost.

A more recent overview of gantries for proton and carbon therapy is given by U. Weinrich in "Gantry design for proton and carbon hadrontherapy facilities", Proceedings of EPAC 2006 (European Particle Accelerator Conference), Edingburgh, Scotland. As shown, all proton isocentric gantries have longitudinal dimensions between 9 and 12 m and have a maximum radial displacement of the beam from the gantry axis of rotation that varies between 3.2 m and 5 m.

A rotating particle gantry has a rotating beam line which comprises in general a vacuum tube for transporting the particle beam in vacuum, various quadrupole magnets for focussing and defocusing the particle beam, various dipole magnets for bending the particle beam and beam monitors for monitoring the beam. The category of rotating gantries that are addressed in the current application are so-called single plane rotating gantries comprising dipole magnets configured such that the bending in each dipole magnet of the gantry beam line occurs in the same plane. This single plane gantry category distinguishes from another category of gantries, the so-called "cork-screw" gantries which have two orthogonal bending planes. In the category of single plane gantries there currently exist two major configurations which are schematically illustrated in FIG. 1B by showing the central beam paths followed by the beam in these gantries. The beam enters the gantry essentially parallel with the axis of rotation at the coupling point or entrance point 11 and starts with a first straight beam line section before entering a first dipole magnet 12, 13. This coupling point or entrance point is defined as the transition between the fixed part of a beam line and the beam line of the rotating gantry. The difference between the two major configurations of single plane gantries is related to the number of dipole magnets installed in the gantry. The bending plane of the dipoles of a single plane gantry are further called "horizontal" plane and the non-bending plane is called "vertical" plane or Y plane.

The first major configuration in the category of single plane gantries is a so-called conical gantry. An example is the proton gantry built by the applicant and shown in FIG. 1A. The central beam path followed by a proton beam in such a gantry is shown in FIG. 1B as a dotted line. A first 45° dipole magnet 12 bends the beam away from the axis of rotation of the gantry and the beam then further follows a second straight beam line section before entering the second 135° dipole magnet 15 which is bending and directing the beam essentially perpendicular to the axis of rotation. The crossing of the beam and the axis of rotation of the gantry is called the treatment isocenter 17. The target to be irradiated is positioned at the treatment isocenter. In the conical gantry configuration built by the applicant (FIG. 1A), the straight beam line section between the coupling point 11 and the first 45° dipole magnet 12 comprises four quadrupole magnets and the second straight section between the first 12 and second 15 dipole magnet comprises five quadrupole magnets (no quadrupole magnets are shown on FIG. 1B). The conical gantry configuration built by the applicant is also discussed by Pavlovic in "Beam-optics study of the gantry beam delivery system for light-ion cancer therapy", Nucl. Instr. Meth. In Phys. Res. A 399(1997) on page 440.

The second major configuration in the category of single plane gantries is the so-called cylindrical gantry, also named barrel gantry. The central beam path of the beam in a cylindrical gantry is also illustrated in FIG. 1B where the beam, represented by a full line, is entering the gantry at the coupling point 11 and travels through a first straight beam line section before entering the first dipole magnet 13, for example a first 60° magnet, which is bending the beam away from the axis of rotation and is followed by a second straight beam line section before entering the second dipole magnet 14 which has the same bending angle but opposite direction, resulting in a beam propagating in a third straight beam line section that is parallel with the axis of rotation of the gantry. A third 90° dipole magnet 16 is then further used to bend the beam in a direction perpendicular to the axis of rotation. The three straight beam line sections are comprising respectively two, two and three quadrupole magnets (not shown on FIG. 1B). This cylindrical gantry configuration illustrated in FIG. 1B corresponds to the geometry proposed for the PSI proton Gantry 2 which is discussed by Weinrich (p 966-967 and FIG. 8 p 966). From all isocentric gantry configurations discussed by Weinrich, the gantry with the smallest maximum radial beam displacement from the rotation axis of the gantry (which will further be named gantry radius), is obtained by the design proposed for the isocentric PSI proton Gantry 2 as discussed above. With this geometry a gantry radius of 3.2 m is obtained (last column of Table 2 page 967).

A variant of the cylindrical gantry is the so-called oblique gantry disclosed by M. Pavlovic in "Oblique gantry—an alternative solution for a beam delivery system for heavy-ion cancer therapy", Nucl. Instr. Meth. in Phys. Res. A 434 (1999) on page 454-466. As is the case for a standard cylindrical gantry, this oblique gantry also comprises three dipole magnets whereof the first two dipole magnets have the same bending angles but of opposite signs, resulting in a beam propagating in a direction between the second and third dipole that is parallel with the axis of rotation of the gantry (see Pavlovic et al, FIG. 3 on page 460). The third dipole magnet has an angle smaller than 90° (e.g. 60°) and as a result the final beam is not delivered perpendicular to the axis of rotation of the gantry as is the case for the standard cylindrical gantry described above. Instead, the final beam is delivered at isocenter under an angle with respect to the gantry axis that is different from 90°. For example, the beam is delivered under an angle of 60° in case the bending angle of the third dipole magnet is 60°. The disadvantage of such an oblique gantry is that one can not cover all treatment angles without moving the patient. For example, for a 60° oblique gantry, the treatment angle is limited to a −60° to +60° sector (see page 463, section 4, first sentence).

In EP1041579A1, additional examples of cylindrical gantry configurations are disclosed. In FIG. 1 of this patent application, a cylindrical gantry is shown and as specified in Table 2: the first and second dipole magnets have a bending angle of 42° and the third dipole magnet has a bending angle of 90°. As mentioned in the abstract of this patent application, other configurations are anticipated, namely a first dipole magnet having a bending angle in the range of 40° to 45° and second dipole magnet having a bending angle identical to the first dipole magnet for bending the beam parallel to the axis of rotation of the gantry. The third bending magnet has a bending angle in the range of 45° to 90° for bending the beam towards and intersection of the beam with the axis of rotation of the gantry. As discussed above, if the last bending magnet has a bending angle smaller than 90° (this is the so called oblique gantry), the beam is not delivered perpendicular to the axis of rotation of the gantry. Again the disadvantage of such an oblique gantry configuration is that not all treatment angles can be covered.

Both the conical gantry developed by the applicant and shown in FIG. 1A and the cylindrical gantry configuration of the PSI gantry 2 (see Weinrich FIG. 8 p 966) were designed for use with a pencil beam scanning system. In the 45°-135° conical gantry configuration, the scanning magnets 18 for scanning the beam in the horizontal plane (also called X direction) and the vertical plane (also called Y direction) are installed downstream from the 135° dipole magnet. A disadvantage of such a gantry configuration is that a large spacing needs to be provided between the exit of the last bending magnet (in this example, the 135° magnet) and the gantry isocenter which results in a large gantry radius R. The scanning magnets need to be installed far enough from the isocenter (e.g. 2 m or more) in order to have a sufficiently large SAD (Source to Axis Distance). The larger the SAD the smaller is the skin dose. As shown in FIG. 1B, the gantry radius, defined as the maximum distance of the beam to the axis of rotation of the gantry, is about 4.5 m for this conical gantry.

In the cylindrical PSI gantry 2 configuration, the scanning magnets 18 are installed between the second 60° dipole magnet 14 and the last 90° dipole magnet 16. A major disadvantage of this gantry configuration is that the last 90° bending magnet 16 needs to have a large gap (vertical) and a large pole width (horizontal) in order to be able to scan the beam over a large target area at isocenter (e.g. 25 cm×20 cm or 40 cm×30 cm). As a consequence, the size and weight of such a 90° dipole magnet is large and moreover the power consumption is high. Such a 90° magnet can weight as much as 20 tons. A second disadvantage is that the straight parallel section between the second 60° dipole magnet and the last 90° bending magnet is relatively long which results in long axial gantry dimensions. This PSI gantry 2 has an axial length, defined as the axial distance between the coupling point 11 and the isocenter, of 11.6 m as described by Weinrich (Table 2, p 966). Such a cylindrical gantry configuration with a 90° last bending magnet is also discussed in U.S. Pat. No. 7,348, 579.

The present invention aims to provide a device which overcomes the problems of the prior art. It is an objective of the present invention to design a gantry that can be built at a reduced cost compared to the prior art gantries and where the power consumption of the last dipole magnet is reduced. An additional objective is also to reduce the overall size of the gantry, so that the volume of the treatment room and hence the cost of the building can be reduced as well.

SUMMARY OF THE INVENTION

The present invention is set forth and characterized by the appended claims.

According to a first aspect of the invention, an isocentric gantry designed for rotating around an axis of rotation and for delivering a particle beam for use in particle therapy is provided. This isocentric gantry is comprising:
- a gantry beam line having a gantry entrance point for entering said particle beam into the gantry in a direction essentially parallel with the axis of rotation;
- a first, a second and a third dipole magnet sequentially arranged for successively bending the particle beam in a single plane and for delivering said particle beam at an isocenter in a direction essentially perpendicular to the axis of rotation;

quadrupole magnets for focussing and defocusing said particle beam;

and said isocentric gantry is further characterized in that said third dipole magnet has a bending angle smaller than 90°, preferably smaller than 80°, more preferably smaller than 70°.

Most preferably, the third dipole magnet has a bending angle of 60°.

More preferably, a beam line section between said gantry entrance point and an entrance of the first dipole magnet is a short drift section. This means that between the entrance point and the entrance of the first dipole magnet no quadrupole magnets are installed.

Even more preferably, the beam line section between said first and said second dipole magnet comprises five quadrupole magnets and the beam line section between said second and said third dipole magnet comprises no quadrupole magnet.

Even more preferably, the isocentric gantry is comprising means for rotating the gantry over an angular range of at least 180°.

The gantry according to the invention may further comprise, either particle beam scanning means installed between said second dipole magnet and said third dipole magnet and configured for scanning said particle beam over a target area at the isocenter, or particle beam scattering means adapted to provide a broad beam at the isocenter.

According to a second aspect of the invention a particle therapy apparatus is provided, comprising a particle accelerator, means for varying the particle energy, a beam transport system and an isocentric gantry according to the first aspect of the invention.

DETAILED DESCRIPTION OF PREFERRED EMBODIMENTS OF THE PRESENT INVENTION

The present invention will now be described in detail in relation to the appended drawings. However, it is evident that a person skilled in the art may conceive several equivalent embodiments or other ways of executing the present invention.

Figure 1A:
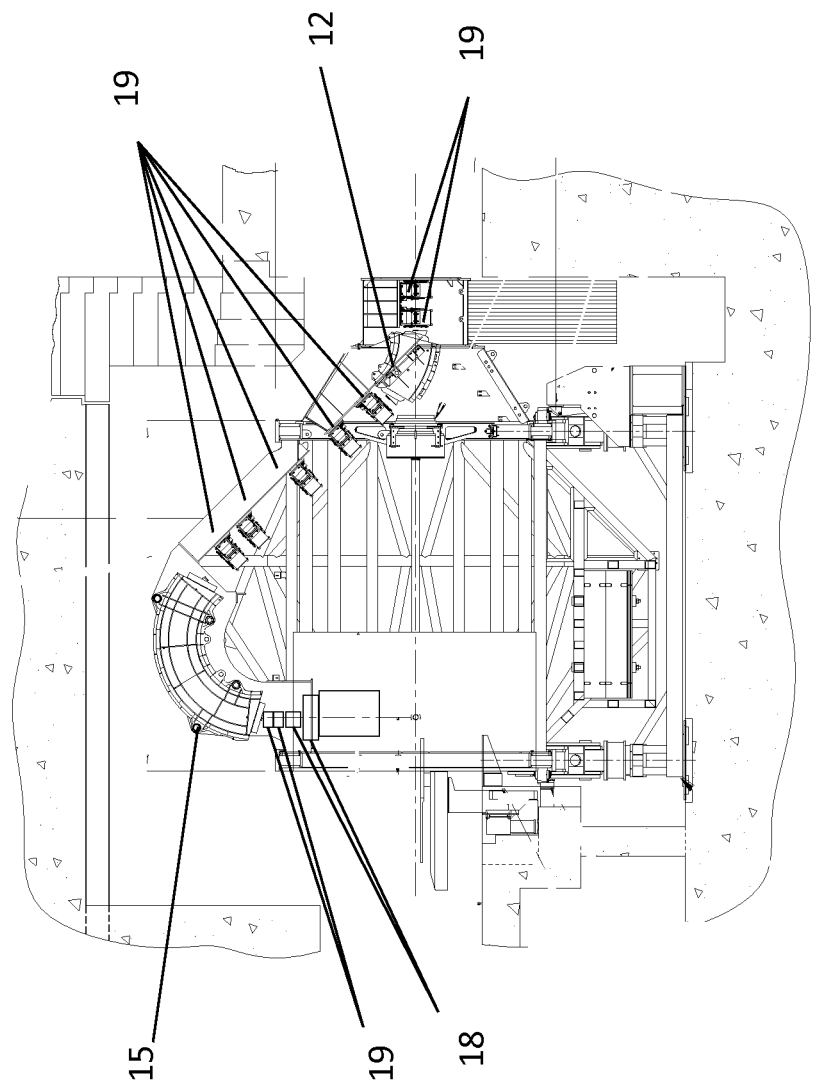
FIG. 1A shows a representation of a prior art gantry configuration.
Figure 1B:
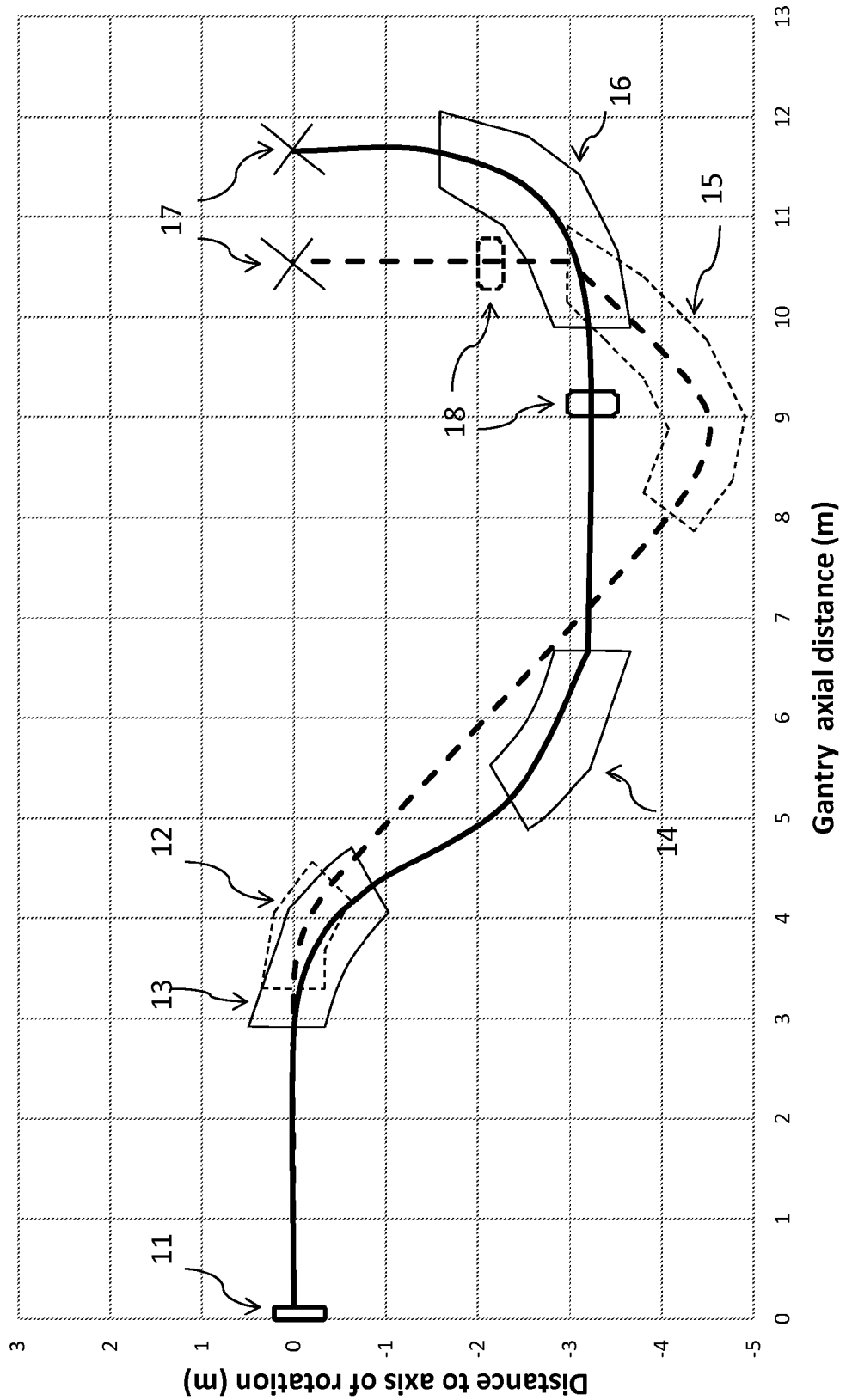
FIG. 1B shows a schematic representation of trajectories followed by a particle beam for two prior art gantry configurations.
Figure 2:
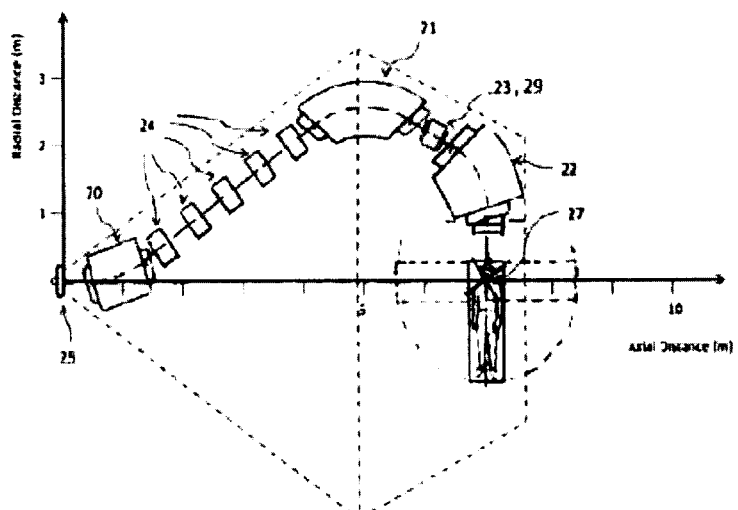
FIG. 2 shows a schematic representation of a layout of an exemplary gantry according to the invention.

First, an exemplary single plane gantry comprising a pencil beam scanning system is disclosed, which is at the same time compact, has a reduced weight, has a reduced production cost and has a lower power consumption. FIG. 2 shows a preferred layout of such a gantry. The gantry is represented in a 90° angular position (i.e. when looking in a direction parallel with the gantry axis, from isocenter 27 towards the first dipole magnet 20, the gantry is at three o'clock). The gantry has three dipole magnets 20, 21, 22 and has means 23 for scanning the beam in X and Y which are installed between the second dipole magnet 21 and the third dipole magnet 23. Between the first dipole magnet 20 and the second dipole magnet 21, a number of quadrupole magnets 24 are installed. The beam line section between the gantry entrance point 25 and the entrance of the first dipole magnet 20 is preferably a short drift section comprising no quadrupole magnet. As illustrated in FIG. 2 with the dashed-dotted lines, the overall shape this gantry is describing when rotating can be approximated by a double cone, a first cone having its apex at the level of the coupling point 25 and having a base perpendicular to the gantry axis of rotation and crossing the second dipole magnet 21 at a position where the beam has made a first angular rotation equal to the angle of the first dipole magnet. The second cone is a truncated cone having it base coincide with the base of the first cone and having its apex cut off by a plane parallel with the base plane as illustrated in FIG. 2.

In a preferred embodiment of the invention, the third dipole magnet 22 as a bending angle of 60° and the first dipole magnet 20 has a bending angle of 36°. The bending angle of the second magnet is then calculated to be 36°+90°−60°=66°. Between the second 21 and the third 22 dipole magnet, means for scanning the particle beam in X and Y can be provided. The case being, a combined X-Y scanning magnet is preferably used to that end because it takes less space than two separate scanning magnets for the X and Y direction. The length of the first straight beam line section between the gantry entrance point (25) and the first dipole magnet (20) is about 0.4 m long and is a pure drift section (i.e. no quadrupole magnets are installed in this section). In a preferred embodiment of the invention, five quadrupole magnets are installed between the first 36° dipole magnet 20 and the second 66° dipole magnet 21. The space available for installing these quadrupole magnets, i.e. the length of the straight section between the first and second dipole magnet is about 3.5 m. The length of the straight beam line section between the second 66° dipole magnet and the third 60° dipole magnet is about 0.8 m. The distance between the exit of the 60° last bending magnet 22 and the isocenter 27 is about 1 m which allows sufficient space for installing not only the patient but also to install for example monitor detectors between the exit of the 60° bending dipole 22 and the patient (e.g. dose monitor detectors and/or beam positioning monitor detectors). The main characteristics of a magnet designed for use as the last dipole magnet 22 of the gantry according to the preferred embodiment of the invention are summarized in Table 1. The example given is for a design for a particle beam with magnetic rigidity of 2.3 Tm (e.g. 235 MeV of protons). To limit the power consumption, this magnet uses large cross section, saddle shaped coils (also known as bedstead coils).

As shown in Table 1, the weight of the magnet is about 9.17 tons (including 2.05 tons from the coils) and the total magnet power at a beam energy of 235 MeV is 226 kW. This 60° dipole magnet has pole faces rotated by 17° in order to provide additional vertical focussing as will be discussed below.

TABLE 1

| General characteristics | Value | Unit |
| --- | --- | --- |
| Deflection angle | 60 | ° |
| Pole face rotation | 17 | ° |
| Bending radius | 120 | cm |
| Gap (vertical) | 20.00 | cm |
| Pole width (horizontal) | 22.00 | cm |
| Coil radial thickness | 25.00 | cm |
| Flux return thickness | 24 | cm |
| Average field | 1.92 | T |
| Total height of coils | 35.00 | cm |
| Pole thickness | 7.50 | cm |
| Total magnet height | 83.00 | cm |
| Steel weight | 6866.97 | kg |
| Weight of one coil | 1024.4 | kg |
| Total weight | 9.17 | Tons |
| Total power | 225.3 | kW |

A preferred gantry beam optics for the gantry shown in FIG. 2 is now further discussed. The gantry entrance, at the level of the coupling point 25, is defined at 0.4 m downstream from the entrance of the first dipole magnet 20. At the gantry entrance the beam must have the same emittance in X and Y in order to have a gantry beam optics solution that is independent from the gantry rotation angle. X and Y axis are here defined as the crossing of a plane perpendicular to the axis of the central beam trajectory with the horizontal plane and vertical plane, respectively. In addition to the same emittance in X and Y, a waist of identical size in X and Y is specified at the entry point 25. Starting with these beam conditions at the gantry entrance, a set of additional conditions need to be met:

1. At the isocenter 27, the beam must have a small waist, of identical size in X and Y.
2. The gantry beam-optical system must be double achromatic, i.e. the beam imaging properties must be independent from momentum (dispersionless) and independent from position.
3. The maximum size of the beam (one sigma) inside the quadrupoles should not exceed 2 cm in order to keep a reasonable transmission efficiency in the gantry.

Figure 3:
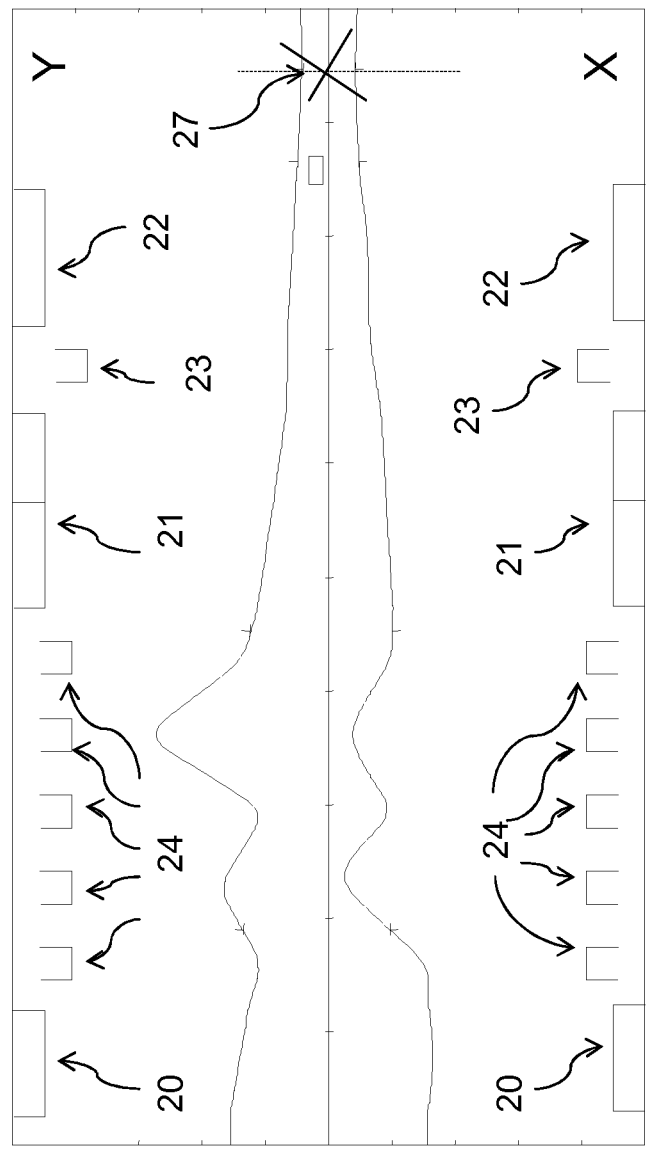
FIG. 3 shows results of a beam optics calculation for the gantry of FIG. 2.

In order to meet these various optical conditions the magnetic field in the five quadrupole magnets installed between the first and second dipole magnet are defined. Other parameters that can be used to find an optimum optical solution are the angles of the pole faces of the dipole magnets. A beam optics calculation is made for a proton beam of 170 MeV. The bending radius for the first and second dipole magnet are specified to 1.5 m. At the gantry entrance point one starts with a circular beam having a double waist with size of 12.5 mm and a divergence of 0.6 mrad. This size and divergence corresponds with an emittance of 7.5 Pi mm mrad, which is a typical value of the beam emittance obtained with current proton therapy systems developed by the applicant. For the 36° first dipole magnet a rectangular pole was adopted (pole faces rotated by 18°) and for the 66° second dipole magnet a pole face rotation of 15° and 21° is used for the entrance and exit, respectively. The resulting beam trajectory in X and Y calculated with the beam optics TRANSPORT code is shown in FIG. 3. Information on the TRANSPORT code can be found in D. C. Carey, K. L. Brown and F. Rothacker, "Third-Order TRANSPORT—A Computer Program for Designing Charged Particle Beam Transport Systems," SLAC-R-95-462 (1995). The relative beam positions with respect to the central beam trajectory are plotted for the X direction and Y direction in the lower panel and upper panel of FIG. 3, respectively. The positions along the beam path of the quadruopole magnets 24 and dipole magnets 20, 21, 22 are indicated. In FIG. 3, the position of the scanning magnets 23 is represented only for information purposes; in this calculation the scanning magnets are off (the effect of the scanning magnets will be discussed below). At the isocenter 27, a circular beam spot, with an X and Y waist having a size of about 3.5 mm and a divergence of about 2.2 mrad is obtained which is a beam size adequate for pencil beam scanning. This beam optical solution also fulfils the conditions of a double achromat.

Figure 4:
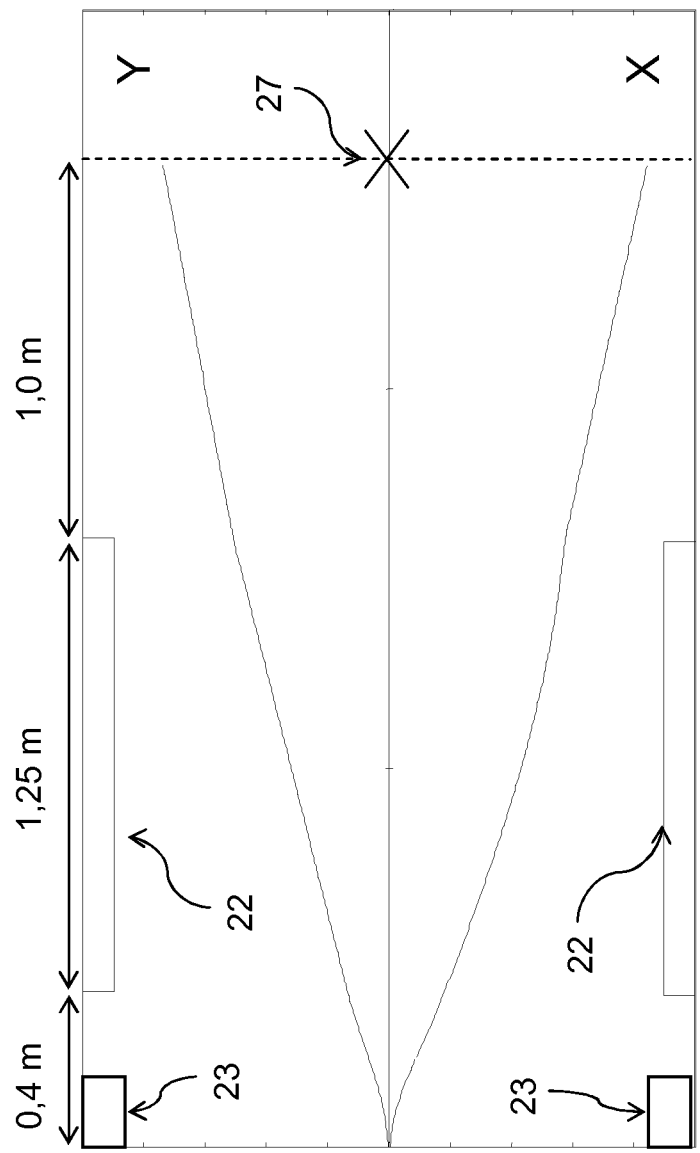
FIG. 4 shows results of a beam optics calculation while scanning the beam in the gantry of FIG. 2.

Besides the need to obtain a beam spot size at isocenter that is suitable for use in pencil beam scanning, one also has to make sure that with the proposed beam line geometry a large scanning area at isocenter can be obtained. The adapted specifications for field sizes are that a field of 25 cm (X)×20 cm (Y) needs to be covered at the isocentric plane and preferentially a sufficiently large SAD (i.e. equal or larger than 2 m) is required. The beam line geometry shown in FIG. 2 and the beam optical solution presented in FIG. 3 fulfils these requirements with respect to field size and SAD. This is demonstrated in FIG. 4 where the trajectory of a 170 MeV proton beam when travelling between the scanning magnets and the isocenter is calculated while the beam is being scanned at a maximum amplitude in X and Y. In this calculation, the scanning magnets are deflecting the beam by 66 mrad in X and 50 mrad in Y, respectively, which are considered as moderate bending angles that can easily be obtained with known scanning magnet technology. In FIG. 4 the positions of the scanning magnet 23 in X and Y, the 60° last dipole magnet 22 and the isocenter 27 are shown. The specifications of the 60° dipole concerning pole edges, bending radius, gap and pole width are these given in Table 1. The distance between the center of the scanning magnet and the entrance of the 60° dipole magnet is about 0.4 m, the central beam travel length in the 60° dipole is about 1.25 m and the distance between the exit of the 60° dipole and the isocenter is taken to be 1.0 m. The calculations show that, at the isocentric plane perpendicular to the central beam, the beam size is 25 cm in X and 22 cm in Y and the beam size at the exit of the 60° dipole magnet is 17.2 cm in X and 15.2 cm in Y, respectively. One can then calculate the virtual SAD, i.e. the SAD obtained as if the beam would have originated from a point source without any magnetic element between the point source and the isocenter. With the geometry proposed, this results in a virtual SAD in X and Y that is larger than 3 m.

Figure 5:
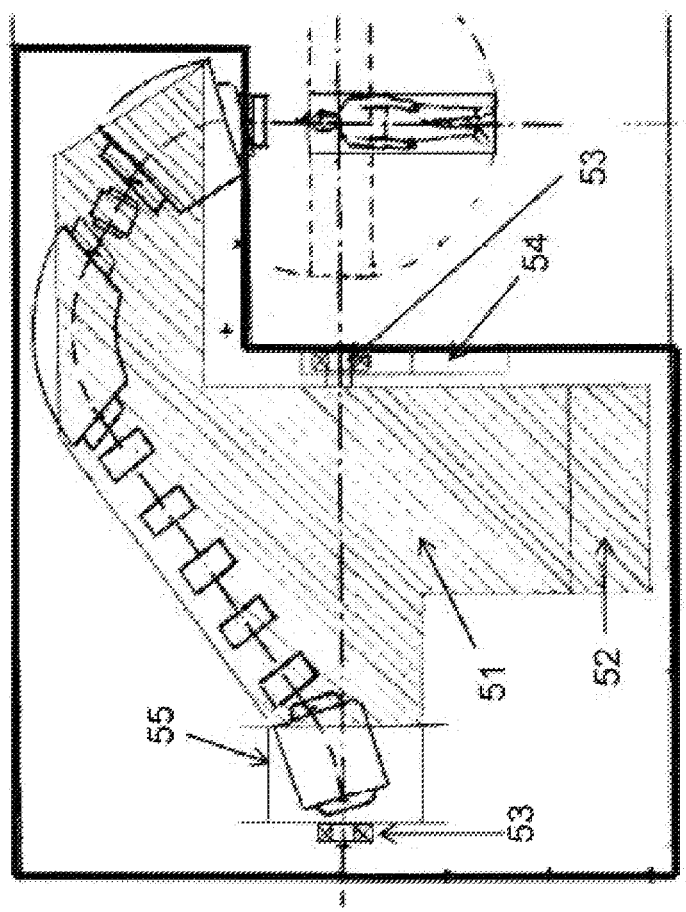
FIG. 5 shows a conceptual view of an exemplary gantry mechanical structure according to the invention.

An exemplary gantry mechanical conceptual design supporting a double cone gantry according to the invention is now discussed and schematically illustrated on FIG. 5. A plane structure made of for example metallic girders 51 can be used to sandwich all the magnets of the gantry together with a counterweight 52. Two standard commercial self-aligning spherical roller bearings 53 are used as rotating means. For the second roller bearing, on the patient side, a cantilevered fixed structure 54 is used for supporting the main roller bearing while allowing the gantry structure to come under the bearing to reach extreme gantry angles, up to 180° (beam vertical upward). At the level of the first dipole magnet, a drum structure 55 is installed for supporting the cable spool. In addition, not shown on FIG. 5, the gantry is equipped with a gantry drive and braking system, consisting of a single motor-gearbox assembly connected to the gantry by a chain drive. An advantage of the gantry configuration according to the invention is that the centre of gravity of the last dipole magnet is closer to the axis of rotation (when compared with for example a gantry configuration based on a last 90° dipole magnet, see FIG. 8 in the publication of Weinrich), which results in reduced constraints for what concerns the mechanical structure (for example the counterweight can be put closer to the axis of rotation reducing the size of the gantry). The gantry can preferentially be rotated by 190°, i.e. depending on the building layout, either a configuration that rotates clockwise from 180° to 10° or a configuration rotating clockwise from 350° to 180° (angles are defined according to IEC International Standard 61217, Radiotherapy equipment—Coordinates, movements and scales, 1996).

This mechanical concept is intended to reduce the costs of the gantry mechanical structure, while allowing good accessibility to the patient. One of the main cost drivers in current gantry structures (such as for example for the conical 45°-135° configuration) is the need to roll the gantry on large, very accurate gantry rings that need to be custom built of high strength, wear resistant steel and which are supported by complex bogies. Other cost drivers are the drive and braking mechanisms done through the gantry bogies rollers and where the torque is severely limited by the rollers slippage, and finally the gantry 3-dimensional frame structure.

Figure 6:
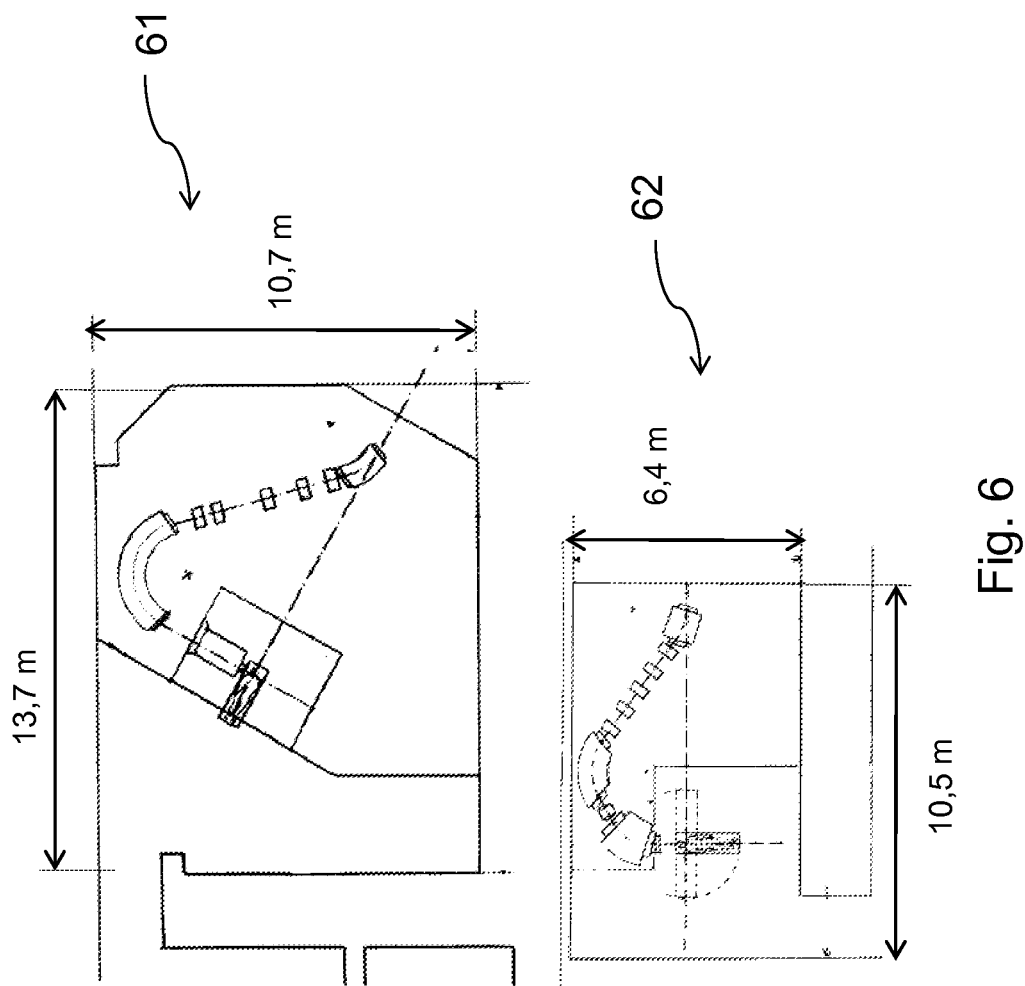
FIG. 6 shows a layout of a treatment room for a prior art gantry together with a treatment room layout for a gantry according to the invention.

A particle therapy apparatus comprises an accelerator producing energetic charged particles, means for varying the particle energy, a beam transport system for guiding the beam to one or more treatment rooms and, for each treatment room, a particle beam delivery system. The particle beam delivery system is either a gantry or a so-called fixed beam delivery system. The gantry treatment rooms are requiring in general a large footprint and building volume. With the gantry design according to the invention a smaller gantry room can be used when compared to for example a conical 45°-135° gantry configuration. This is illustrated in FIG. 6 where, at the same scale, a footprint 61 of a treatment room comprising a conical gantry is shown together with a footprint 62 of a treatment room comprising an exemplary double cone compact gantry according to the invention. With the gantry according to the invention, a gantry treatment room having a footprint of 10.5 m by 6.4 m can be used as shown on FIG. 6, whereas the current gantry treatment rooms using a conical 45°-135° configuration, as provided by the applicant, require a footprint of 13.7 m by 10.7 m.

Figure 7:
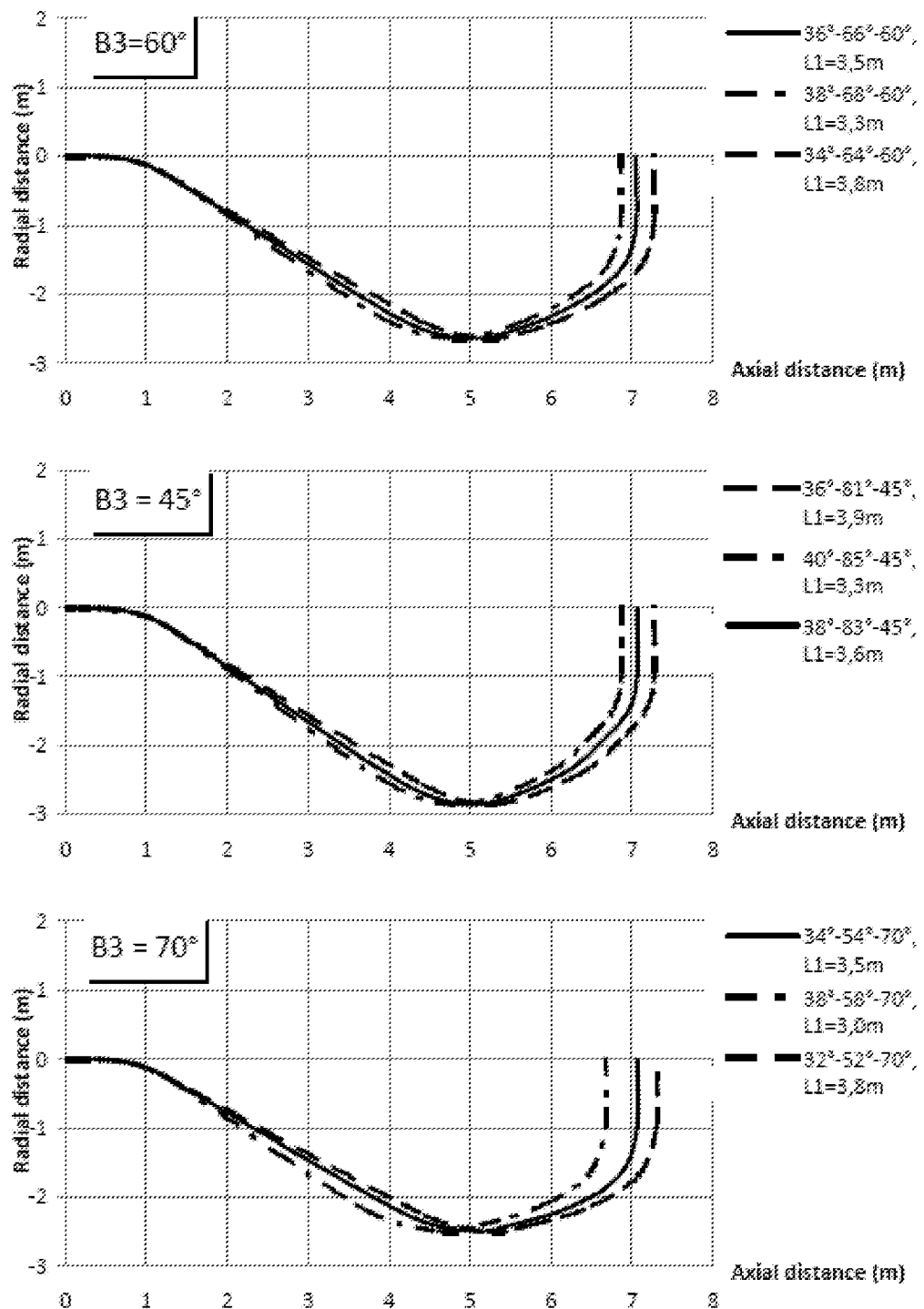
FIG. 7 shows the central beam path followed by a proton beam for various gantry configurations according to the invention.

It is now discussed how geometrical dimensions such as gantry radius and gantry length are influenced by changing certain parameters of the preferred gantry configuration. With the preferred gantry configuration of the invention, comprising three dipoles of respectively 36° (=B1), 66° (=B2) and 60° (=B3), the length of the gantry, defined as the axial distance between the coupling point 25 and the isocenter 27, is about 7.05 m and the gantry radius, defined as the maximum distance of the central beam trajectory to the gantry axis of rotation, is about 2.64 m. This radius is in fact defined by on one hand the selection of the bending angle of the last dipole magnet 22 and on the other hand by the spacing between the exit of the last dipole magnet 22 and the isocenter (isocenter clearance) and the spacing between the second dipole magnet 21 and the last third dipole magnet 22 (B2-B3 spacing). In the preferred geometry these spacings are equal to about 1 m (isocenter clearance) and to about 0.8 m (B2-B3 spacing). When the radius of the gantry is defined in this way, the only parameter that is further influencing the length of the gantry is the choice of the bending angle of the first dipole magnet. Once the bending angle of the first dipole magnet and the gantry radius are specified, the distance L1 between the first dipole magnet 20 and the second dipole magnet 21 is also fixed. In the preferred geometry, this distance is about 3.5 m. Of course other embodiments can be realized by adjusting these parameters defining the gantry geometry. For example, the top panel of FIG. 7 shows the geometry of the preferred 36°-66°-60° configuration. One can for example slightly increase or decrease the angle of the first dipole magnet 20 which results in a decrease and increase, respectively, of the gantry length as shown on the figure. The corresponding changes in the value of the distance L1 is mentioned on the figure. In the middle panel of FIG. 7 the angle of the last bending magnet has been set to 45° while keeping the same isocenter clearance and distance B2-B3 as in the B3=60° configuration. As a consequence of the reduction of the bending angle of the last dipole magnet 22, the gantry radius is increased by about 0.2 m. With a 38° (B1)-83° (B2)-45° (B3) gantry configuration the length of the gantry is maintained at about 7 m. In the third panel of FIG. 7, the angle of the last dipole magnet is set to 70°. When keeping the isocenter clearance and the B2-B3 spacing equal to the values of the previous cases, due to the larger bending angle of B3, the gantry radius is decreased with about 0.15 m when compared to the preferred solution. With a 34° (B1)-54° (B2)-70° (B3) configuration the gantry length is about 7 m.

The optimum double cone gantry configuration is a compromise between on the one hand the technical feasibility and cost of the last dipole magnet 22 and on the other hand between the maximum dimensions (gantry radius, gantry length) acceptable. A good compromise is for example the selection of a 60° last dipole magnet 22 with the specifications given in Table 1 which can be built at reasonable cost and which has a major reduction in size and weight when compared to for example a 90° last dipole magnet as used in the prior art. As discussed above, this preferred solution fits in a treatment room foot print of 6.4 m by 10.5 m as was illustrated in FIG. 6. However, the person skilled in the art will recognize that the advantage of the invention will be obtained from as soon as the last dipole magnet 22 has a bending angle smaller than 90°. Preferably, the last dipole magnet 22 has a bending angle smaller than 80°. More preferably, the last dipole magnet 22 has a bending angle smaller than 70°.

The above description concerns a gantry comprising particle beam scanning means 23. Alternatively, the gantry according to the invention may further comprise particle beam scattering means which are adapted to provide a broad beam at the isocenter 27. By a "broad beam", it must be understood a beam having dimensions in the X-Y plane which 10 substantially correspond to the size of the target in the X-Y plane. Scattering means for providing such broad beams have been described by Chu et al. in "Instrumentation for treatment of cancer using proton and light-ion beams", Rev. Sci. Instrum. 64(8) August 1993, pages 2074 to 2084. A broad beam can for example be obtained with a so-called double scattering beam delivery system and typically comprises the following components: a first scatterer (e.g. set of foils), a second scatterer, a beam modulator (e.g. range modulator wheel or ridge filter), an aperture and range compensator. In a classical gantry providing broad beams, the various components of the scattering beam delivery system are installed downstream of the last dipole magnet 22. However, to integrate a scattering beam delivery system into a compact gantry according to the invention, some components of the scattering means are preferably installed upstream of the last dipole magnet 22. For instance, when adopting a double scattering system, the first scatterer 29 is preferably installed between the second dipole magnet 21 and the third (last) dipole magnet 22. Other components such as for example a ridge filter are preferably installed after the third dipole magnet 22.

Although the embodiments described are focussing on proton gantries, the invention is not limited to proton gantries. The person skilled in the art can easily apply the gantry geometry according to the invention to gantries for use with any type of charged particles such as e.g. a gantry for carbon ions or other light ions. The same beam optical configuration is applicable independently of the magnetic rigidity of the beam; one simply has to scale the magnetic fields in the various magnets of the beam line.

Gantries for particle therapy have been designed since many years but so far no solution has been proposed to address the problems of the prior art gantry designs. According to the present invention a new gantry design is provided resulting in remarkable results that provide a solution to overcome the problems of the prior art. The new gantry design according to the invention has major advantages compared to the current gantry designs (e.g. conical gantries, cylindrical gantries, . . . ).

Compared to the conical gantries, the following major advantages obtained with the gantry according to the invention can be distinguished:
- Diameter and length of the gantry are strongly reduced
- The heavy gantry elements are positioned closer to the axis of rotation
- The mechanical gantry configuration is less expensive Compared to the cylindrical gantries (e.g. PSI 2 gantry or Heidelberg carbon gantry as discussed by Weinrich on pages 966 (FIG. 8) and pages 967 to 968, respectively) the following major advantages obtained with the gantry according to the invention can be distinguished:
- The last bending magnet with large gap and large pole surfaces is less heavy and has a smaller energy consumption
- The centre of gravity of the last bending magnet is closer to the axis of rotation resulting in less mechanical constraints for the gantry mechanical structure
- In case of a scanning configuration, less powerful scanning magnets are needed to cover a same given scanning area at isocenter.

The invention claimed is:

1. An isocentric gantry designed for rotating around an axis of rotation and for delivering a particle beam for use in particle therapy, comprising:
   - a gantry beam line having a gantry entrance point for entering said particle beam into the gantry in a direction essentially parallel with the axis of rotation;
   - bending means for bending the particle beam in a single plane and delivering said particle beam at an isocenter in a direction essentially perpendicular to the axis of rotation, wherein said bending means include:
     - first bending means configured for bending the particle beam away from said axis of rotation,
     - second bending means configured for bending the particle beam towards the axis of rotation, and
     - third bending means configured for bending the particle beam to said direction essentially perpendicular to the axis of rotation, said third bending means having a bending angle smaller than 80°; and
   - particle beam scanning means installed in the beam line and configured for scanning said particle beam in both X and Y directions over a target area at the isocenter, wherein the scanning means is located between the second and the third bending means.

2. The isocentric gantry of claim 1, wherein the bending means comprise dipole magnets.

3. The isocentric gantry of claim 1, wherein the bending means consists of 3 dipole magnets, where the first dipole magnet bends the beam away from said axis of rotation, the second dipole magnet bends the beam towards the axis of rotation, and the third dipole magnet bends the beam to said direction essentially perpendicular to the axis of rotation and by an angle smaller than 80°.

4. The isocentric gantry of claim 1, wherein the third bending means has a bending angle of 60°.

5. The isocentric gantry of claim 3, further comprising quadrupole magnets in the beam line section between the first and second dipole magnet, and wherein the beam line section between the second and the third dipole magnet has no quadrupole magnets.

6. The isocentric gantry of claim 1, further comprising means for rotating said gantry over an angular range of at least 180°.

7. The isocentric gantry of claim 1, wherein the particle beam scanning means comprises a combined X-Y scanning magnet.

8. An isocentric gantry designed for rotating around an axis of rotation and for delivering a particle beam for use in particle therapy, comprising:
   - a gantry beam line having a gantry entrance point for entering said particle beam into the gantry in a direction essentially parallel with the axis of rotation;
   - a sequence of dipole magnets arranged for bending the particle beam in a single plane and delivering said particle beam at an isocenter in a direction essentially perpendicular to the axis of rotation,
   - quadrupole magnets for focusing and defocusing said particle beam; and
   - a first scatterer and a second scatterer installed in the beam line and adapted to provide a broad beam in both X and Y directions at the isocenter, the first scatterer being located between two dipole magnets of said sequence of dipole magnets,
   - wherein in said sequence of dipole magnets, the sum of the bending angles of the dipole magnet or magnets which are located downstream of the first scatterer is smaller than 80°;
   - wherein the sequence of dipole magnets comprises a first dipole magnet configured to bend the particle beam away from said axis of rotation, a second dipole magnet configured to bend the particle beam towards the axis of rotation, and a third dipole magnet configured to bend the particle beam to said direction essentially perpendicular to the axis of rotation, said third dipole magnet having a bending angle smaller than 80°, and
   - wherein the first scatterer is installed between said second dipole magnet and said third dipole magnet and the second scatterer is installed after said third dipole magnet.

9. The isocentric gantry of claim 8, wherein the third dipole magnet has a bending angle of 60°.

10. A particle therapy method for delivering a particle beam to a target by an isocentric gantry designed for rotating around an axis of rotation and for delivering the particle beam to the target in a direction essentially perpendicular to the axis of rotation, comprising the steps:
    - providing a particle beam at an entrance point of said gantry, in a direction essentially parallel with the axis of rotation;
    - bending the particle beam, downstream of the entrance point, within the gantry, to a direction away from the axis of rotation;
    - bending the particle beam, downstream of the bending to a direction away from the axis of rotation, within the gantry, to a direction towards the axis of rotation;
    - scanning the particle beam, downstream of the bending to a direction towards the axis of rotation, within the gantry in both X and Y directions; and,
    - bending the particle beam, downstream of scanning the particle beam in the X and Y directions, within the gantry, by a total angle smaller than 80° and greater than 0°.

11. The method of claim 10, wherein the steps of bending the particle beam are performed with dipole magnets.

12. The method of claim 10, wherein the step of bending the particle beam by a total angle smaller than 80° is a step of bending the particle beam by a total angle of 60°.

13. The method of claim 10, further comprising providing quadrupole magnets between the step of bending the particle beam to a direction away from the axis of rotation and the step of bending the particle beam to a direction towards the axis of rotation.

14. The method of claim 10, further comprising providing means for rotating said gantry over an angular range of at least 180°.

15. An isocentric gantry designed for rotating around an axis of rotation and for delivering a particle beam for use in particle therapy, comprising:
 a gantry beam line having a gantry entrance point for entering said particle beam into the gantry in a direction essentially parallel with the axis of rotation;
 a sequence of dipole magnets arranged for bending the particle beam in a single plane and for delivering said particle beam at an isocenter in a direction essentially perpendicular to the axis of rotation,
 quadrupole magnets for focussing and defocusing said particle beam; and
 particle beam scanning means installed between two dipole magnets of the sequence of dipole magnets and configured for scanning said particle beam in both X and Y directions over a target area at the isocenter,
 wherein in said sequence of dipole magnets, the sum of the bending angles of the dipole magnets which are located downstream of said particle beam scanning means is smaller than 80°.

16. The isocentric gantry of claim 15, wherein the sequence of dipole magnets consists of a first, a second, and a third dipole magnet, where the first dipole magnet bends the beam away from said axis of rotation, the second dipole magnet bends the beam towards the axis of rotation, and the third dipole magnet bends the beam to said direction essentially perpendicular to the axis of rotation and by an angle smaller than 80°.

17. The isocentric gantry of claim 16, wherein the third dipole magnet has a bending angle of 60°.

18. The isocentric gantry of claim 15, further comprising quadrupole magnets between the beam line section between the first and second dipole magnet, and wherein the beam line section between the second and the third dipole magnet has no quadrupole magnets.

19. The isocentric gantry of claim 15, further comprising means for rotating said gantry over an angular range of at least 180°.

20. The isocentric gantry of claim 15, wherein the particle beam scanning means comprises a combined X-Y scanning magnet.

21. The isocentric gantry of claim 16, wherein the particle beam scanning means comprises a combined X-Y scanning magnet.

* * * * *